US012150894B2

(12) United States Patent
Govari et al.

(10) Patent No.: US 12,150,894 B2
(45) Date of Patent: Nov. 26, 2024

(54) EVALUATION OF PHACOEMULSIFICATION DEVICES

(71) Applicant: JOHNSON & JOHNSON SURGICAL VISION, INC., Santa Ana, CA (US)

(72) Inventors: Assaf Govari, Haifa (IL); Yehuda Algawi, Binyamina (IL); Amit Fuchs, Hogla (IL); Eran Aharon, Haifa (IL); Ilya Sitnitsky, Nahariya (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 648 days.

(21) Appl. No.: 17/236,221

(22) Filed: Apr. 21, 2021

(65) Prior Publication Data

US 2022/0339032 A1 Oct. 27, 2022

(51) Int. Cl.
*A61F 9/007* (2006.01)
*A61B 17/00* (2006.01)
(Continued)

(52) U.S. Cl.
CPC .......... *A61F 9/00745* (2013.01); *A61M 1/67* (2021.05); *A61M 1/81* (2021.05);
(Continued)

(58) Field of Classification Search
CPC ....... A61F 9/00745; A61M 1/67; A61M 1/81; A61M 3/0283; A61M 2205/3331; A61M 2210/0612; A61B 2017/00725
See application file for complete search history.

(56) References Cited

U.S. PATENT DOCUMENTS 7,644,603 B2 * 1/2010 Gordon ............... A61F 9/00745
73/1.57
2003/0028147 A1 2/2003 Aves et al.
(Continued)

FOREIGN PATENT DOCUMENTS

WO WO-2007001929 A2 * 1/2007 ............... A61B 3/16
WO 2009076717 A1 6/2009
WO 2013085745 A1 6/2013

OTHER PUBLICATIONS

English Translation of WO-2007001929-A2 (Year: 2007).*
(Continued)

*Primary Examiner* — Ryan D Walsh
(74) *Attorney, Agent, or Firm* — Johnson & Johnson Surgical Vision, Inc.

(57) ABSTRACT

A phacoemulsification simulation apparatus includes a trigger device, at least two sensors, and a processor. The trigger device configured to apply, to fluid at an inlet of a needle of a phacoemulsifier, a pressure profile as a function of time in response to an input waveform. The at least two sensors are configured to measure a pressure of the fluid at respective points in the phacoemulsification simulation apparatus. The processor is configured to (a) drive the trigger device with the input waveform, thereby causing the trigger device to apply the pressure profile to the inlet while the fluid is aspirated via an aspiration line, (b) receive measurements of the pressure of the fluid from the at least two sensors, and (c) analyze an aspiration performance of the phacoemulsifier in response to the measurements.

12 Claims, 3 Drawing Sheets

(51) Int. Cl.
  *A61M 1/00* (2006.01)
  *A61M 3/02* (2006.01)
(52) U.S. Cl.
  CPC .. *A61B 2017/00725* (2013.01); *A61M 3/0283* (2013.01); *A61M 2205/3331* (2013.01); *A61M 2210/0612* (2013.01)

(56) References Cited

U.S. PATENT DOCUMENTS

| | | | |
|---|---|---|---|
| 2008/0312536 | A1 | 12/2008 | Dala-Krishna |
| 2014/0114237 | A1 | 4/2014 | Gordon |
| 2014/0171993 | A1 | 6/2014 | Lynn et al. |
| 2015/0037775 | A1 | 2/2015 | Ottensmeyer et al. |
| 2015/0279239 | A1 | 10/2015 | Chang et al. |
| 2016/0063898 | A1 | 3/2016 | Bernal |
| 2016/0095748 | A1 | 4/2016 | Raney et al. |
| 2016/0128869 | A1 | 5/2016 | Zacharias |
| 2019/0051216 | A1 | 2/2019 | Bernal |
| 2021/0106748 | A1 | 4/2021 | Nirkhe |
| 2022/0008251 | A1* | 1/2022 | Govari .............. A61F 9/00745 |
| 2022/0192876 | A1* | 6/2022 | Algawi ............. A61F 9/00745 |
| 2022/0192878 | A1* | 6/2022 | Algawi ............. A61F 9/00745 |
| 2023/0181359 | A1* | 6/2023 | Govari ................ A61M 1/742 606/107 |
| 2023/0218437 | A1* | 7/2023 | Govari ................... A61M 1/74 604/22 |
| 2023/0346597 | A1* | 11/2023 | Govari .............. A61F 9/00745 |

OTHER PUBLICATIONS

Zacharias, J., "Role of Cavitation In the Phacoemulsification Process," Journal of Cataract & Refractive Surgery, May 2008, vol. 34 (5), pp. 846-852.

Aravena et al., Aqueous volume loss associated with occlusion break surge in phacoemulsifiers from 4 different manufacturers. J Cataract Refract Surg. Jul. 2018;44(7):884-888. doi: 10.1016/j.jcrs. 2018.02.026. Epub Jun. 21, 2018. PMID: 29937366.

Dyk et al., Mechanical model of human eye compliance for volumetric occlusion break surge measurements, Journal of Cataract & Refractive Surgery, vol. 44, Issue 2, 2018, pp. 231-236, ISSN 0886-3350, https://doi.org/10.1016/i.jcrs.2017.10.052.

Packer et al., The physics of phaco: A review, Journal of Cataract & Refractive Surgery, vol. 31, Issue 2, 2005 pp. 424-431, ISSN 0886-3350, https://doi.org/10.1016/j.jcrs.2004.11.027. (https://www.sciencedirect.com/science/article/pii/S0886335004011241).

Serafino et al., "Schlieren visualization of fluid dynamics phenomena during phacosonication in cataract surgery", Proc. SPIE 5580, 26th International Congress on High-Speed Photography and Photonics, (Mar. 17, 2005).

U.S. Appl. No. 16/927,135, filed Jul. 13, 2020, and titled, "Aspiration Bypass Control in a Phacoemulsification Probe,".

U.S. Appl. No. 17/130,409, filed Dec. 22, 2020, and titled, "A Module for Aspiration and Irrigation Control,".

Invitation to Pay Additional Fees and Where Applicable Protest Fee for Application No. PCT/IB2022/053373 mailed Jul. 5, 2022, 17 pages.

* cited by examiner

EVALUATION OF PHACOEMULSIFICATION DEVICES

FIELD OF THE INVENTION

The present invention relates generally to phacoemulsification, and specifically to testing of phacoemulsification systems.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques of testing phacoemulsification systems were proposed in the patent literature. For example, David W. Dyk and Kevin M. Miller describe in a paper titled, "Mechanical model of human eye compliance for volumetric occlusion break surge measurements," LABORATORY SCIENCE, Volume 44 Issue 2 February 2018, changes in volume of fluid pulled from the anterior chamber of enucleated human eyes as a function of time. A mechanical compliance model measured ocular volumetric changes is given in an attempt to characterize the post-occlusion break surge response. A test bed incorporated the mechanical model with a mounted phacoemulsification probe and allowed for simulated occlusion breaks. Surge volume was calculated from a measured displacement.

As another example, Carolina Aravena et al. describe in a paper titled, "Aqueous volume loss associated with occlusion break surge in phacoemulsifiers from 4 different manufacturers," LABORATORY SCIENCE, Volume 44 Issue 7 Jul. 2018, evaluation of aqueous surge volume losses associated with occlusion breaks at varying vacuum limits in tested phacoemulsification systems. The anterior chamber was modeled using the spring eye model. To generate an occlusion, a pneumatic cylinder was actuated through a pair of solenoid valves. An electronic timer relay connected to the solenoid valves ensured full occlusion for 3.5 seconds before automatically signaling the solenoids to reverse and suddenly break occlusion.

SUMMARY OF THE INVENTION

An embodiment of the present invention that is described hereinafter provides a phacoemulsification simulation apparatus including a trigger device, at least two sensors, and a processor. The trigger device configured to apply, to fluid at an inlet of a needle of a phacoemulsifier, a pressure profile as a function of time in response to an input waveform. The at least two sensors are configured to measure a pressure of the fluid at respective points in the phacoemulsification simulation apparatus. The processor is configured to (a) drive the trigger device with the input waveform, thereby causing the trigger device to apply the pressure profile to the inlet while the fluid is aspirated via an aspiration line, (b) receive measurements of the pressure of the fluid from the at least two sensors, and (c) analyze an aspiration performance of the phacoemulsifier in response to the measurements.

In some embodiments, the trigger device includes a piston.

In some embodiments, the phacoemulsification simulation further includes a chamber configured to be filled with the fluid and to receive the needle of the phacoemulsifier fluidly coupled with the aspiration line, wherein the trigger device is fitted within the chamber and configured to apply the pressure profile by applying to the needle a blockage profile as a function of time in response to the input waveform.

In an embodiment, one of the at least two sensors are coupled with the chamber.

In another embodiment, the phacoemulsification simulation apparatus further includes a balloon in fluid communication with the chamber.

In an embodiment, one of the at least two sensors is coupled with the phacoemulsifier.

In another embodiment, one of the at least two sensors is coupled with the aspiration line.

In some embodiments, the processor is configured to analyze the aspiration performance by calculating a time delay between one of respective lowest-pressure and highest-pressure values in the measurements received from the at least two sensors.

There is additionally provided, in accordance with another embodiment of the present invention, a phacoemulsification simulation method including, in a phacoemulsification simulation system, applying, to fluid at an inlet of a needle of a phacoemulsifier, a pressure profile as a function of time in response to an input waveform, by driving a trigger device with the input waveform while the fluid is aspirated via an aspiration line. Using at least two sensors, a pressure of the fluid is measured at respective points in the phacoemulsification simulation system. An aspiration performance of the phacoemulsifier is analyzed in response to the measurements.

There is further provided, in accordance with another embodiment of the present invention, a phacoemulsification simulation system including a jig. The jig includes (i) a chamber configured to be filled with fluid and configured to receive a phacoemulsification needle, the chamber including one or more windows configured for use with a stroboscope to visualize vibration of the phacoemulsification needle, and (ii) a flow generator, which is in fluid communication with the chamber, is configured to generate in the chamber a flow of the fluid that removes cavitation bubbles from a field-of-view of the stroboscope.

In some embodiments, the flow generator includes one of a balloon, a piston, and a pump.

In some embodiments, the flow generator is configured to generate a flow that removes the cavitation bubbles away from the one or more windows.

There is further provided, in accordance with another embodiment of the present invention, a method including, using a stroboscope, visualizing vibration of a phacoemulsification needle inside a chamber filled with fluid, wherein the chamber includes one or more windows configured for use with the stroboscope. Cavitation bubbles are removed from a field-of-view of the stroboscope using a flow generator in fluid communication with the chamber, the flow generator configured to generate in the chamber a flow of the fluid.

In some embodiments, removing the cavitation bubbles includes removing the cavitation bubbles away from a field of view of the stroboscope.

The present invention will be more fully understood from the following detailed description of the embodiments thereof, taken together with the drawings in which:

DETAILED DESCRIPTION OF EMBODIMENTS

Overview

During phacoemulsification of an eye lens, particles are aspirated from the eye while the eye is irrigated with a balanced saline solution to replace aspired fluid. During aspiration some of the particles may occlude the distal end of the needle and/or the aspiration channel. The phacoemulsification system should therefore be designed so that such an occlusion, and in particular its abrupt release (post occlusion surge), does not result in eye trauma. Specifically, when an occlusion is released, a vacuum surge may cause a traumatic fall in intraocular pressure (IOP), and a phacoemulsification system should be designed to minimize such a risk.

A phacoemulsification system may include pressure and/or flow sensors, and active controls, such as processor-controlled valves and/or processor-controlled pumps, respectively, to detect and responsively act to minimize a vacuum surge. However, the effectiveness of any of the sensors and the different controls may vary among phacoemulsification system designs.

Further to the above, an occlusion may change a vibration profile of a needle of a phacoemulsifier of the system. For this reason, modeling the vibration and its change may be facilitated by visually recording the vibration of the needle in a fluid-filled jig using a stroboscope. In practice, however, imaging of the stroboscope may be obstructed by cavitation bubbles generated by the vibration.

Embodiments of the present invention that are described hereinafter provide phacoemulsification simulation systems and jigs that enable a phacoemulsification system designer to simulate a human eye for the purpose of minimizing adverse effects of occlusion and occlusion release.

One disclosed phacoemulsification simulation apparatus enables the simulation of pressure-time changes to an actual eye due to occlusion and occlusion release using an eye-model jig, and to explore means to minimize these changes. In another embodiment, the same phacoemulsification simulation apparatus enables the simulation of pressure-time changes using an electromechanical syringe as a trigger device, to inject a pressure wave into an aspiration line of the apparatus, for example, via an inlet of a phacoemulsifier needle fluidly coupled with the aspiration line. Another disclosed jig has one or more windows for imaging by a stroboscope, and a flow generator, such as a fluid-filled balloon, that is configured to remove cavitation bubbles from the stroboscope's field of view. The jig therefore allows the simulation of vibration profiles of a needle experiencing occlusion and occlusion-release so as to optimize needle vibration in an actual eye.

In the disclosed jigs, an eye model is formed as a closed chamber (e.g., a cylinder), into which a needle of the phacoemulsifier is inserted. The chamber is configured to receive the needle of the phacoemulsifier fluidly coupled with the aspiration line. A flexible balloon is connected to the cylinder, to imitate the eye compliance to pressure changes, and the combination may be filled with fluid simulating the aqueous humor and emulsified lens of the eye. A pressure sensor measures the pressure of the fluid inside the cylinder, which may model an IOP pressure.

The jigs are used with an aspiration pump that includes controls on the vacuum applied by the pump, as described above, to enable the effective measurements of different sensing layouts and controls.

One disclosed phacoemulsification simulation apparatus simulates pressure-time changes using a jig that has a trigger device that can simulate the formation and release of an occlusion. To this end, the trigger device applies to an inlet of the needle a blockage profile as a function of time in response to an input waveform.

In addition, at least two sensors sense occlusion/occlusion release by measuring a pressure of the fluid at respective points in a phacoemulsification simulation system comprising the jig. For example, one sensor may be fitted adjacent to the jig, and another sensor may be fitted at the far end of the aspiration line connected to the jig.

A processor of the phacoemulsification apparatus drives the trigger device with the input waveform, thereby causing the trigger device to apply the blockage profile to the inlet while the fluid is aspirated via the needle. Then, the processor receives measurements of the pressure of the fluid from the sensors. The processor analyzes an aspiration performance in response to the measurements. For example, the processor is configured to analyze the aspiration performance by calculating a delay time between lowest pressure values (i.e., maximal vacuum surge readings) of the measurements. In an embodiment, the processor identifies in the measured pressure waveforms of the sensors, maximum or minimum values $p_1(t_1)$ and $p_2(t_2)$ and obtains the time delay $\Delta t = t_2 - t_1$. The experiment may be repeated to obtain an average time delay $<\Delta t>$ per each two-sensor configuration tested.

A smaller delay time means the system receives earlier indication of a vacuum surge and can initiate a corrective action sooner, to eliminate the vacuum surge before the vacuum lasts long enough to damage the eye. Using the measured delay time, a system can be designed that can largely reduce hazard to an eye from vacuum surge, by locating a sensor at an optimal location, e.g., over an aspiration channel/line, and using its readings to activate one or more valves and/or pumps. For example, a system to reduce a vacuum surge is described in U.S. patent application Ser. No. 16/927,135, filed Jul. 13, 2020, and titled, "Aspiration Bypass Control in a Phacoemulsification Probe," whose disclosure is incorporated herein by reference.

In one case, one of the measurements is made by a distal sensor located at the back of the probe (e.g., handpiece). In this embodiment, the phacoemulsification simulation system and the jig were found to enable a design in which a processor can initiate a control response (e.g., pump and/or valve response) to vacuum surge in less than 4 milliseconds (ms). By reversing the vacuum pump to decrease the vacuum level, and quickly increasing the irrigation flow rate momentarily, the vacuum surge duration time can be reduced to roughly 100-150 ms, compared to 400 ms in current systems, using the pumps alone. At a same time, the IOP is stabilized from its surged vacuum level into a normal IOP. Using valves may further reduce vacuum surge duration to negligible values.

In another disclosed jig, the fluid-filled chamber has one or more windows, and a stroboscope is used to visualize the movement of the distal tip (e.g., needle) of a phacoemulsifier needle inside the chamber. However, the inventors have found that tip movement causes cavitation, generating bubbles that obstruct the stroboscope light, for example by attaching to a jig's windows. In an embodiment of the invention, a liquid-filled balloon is coupled to the chamber. When pressed, the fluid from the balloon blows the bubbles away from the stroboscope's field of view.

System Description

Figure 1:
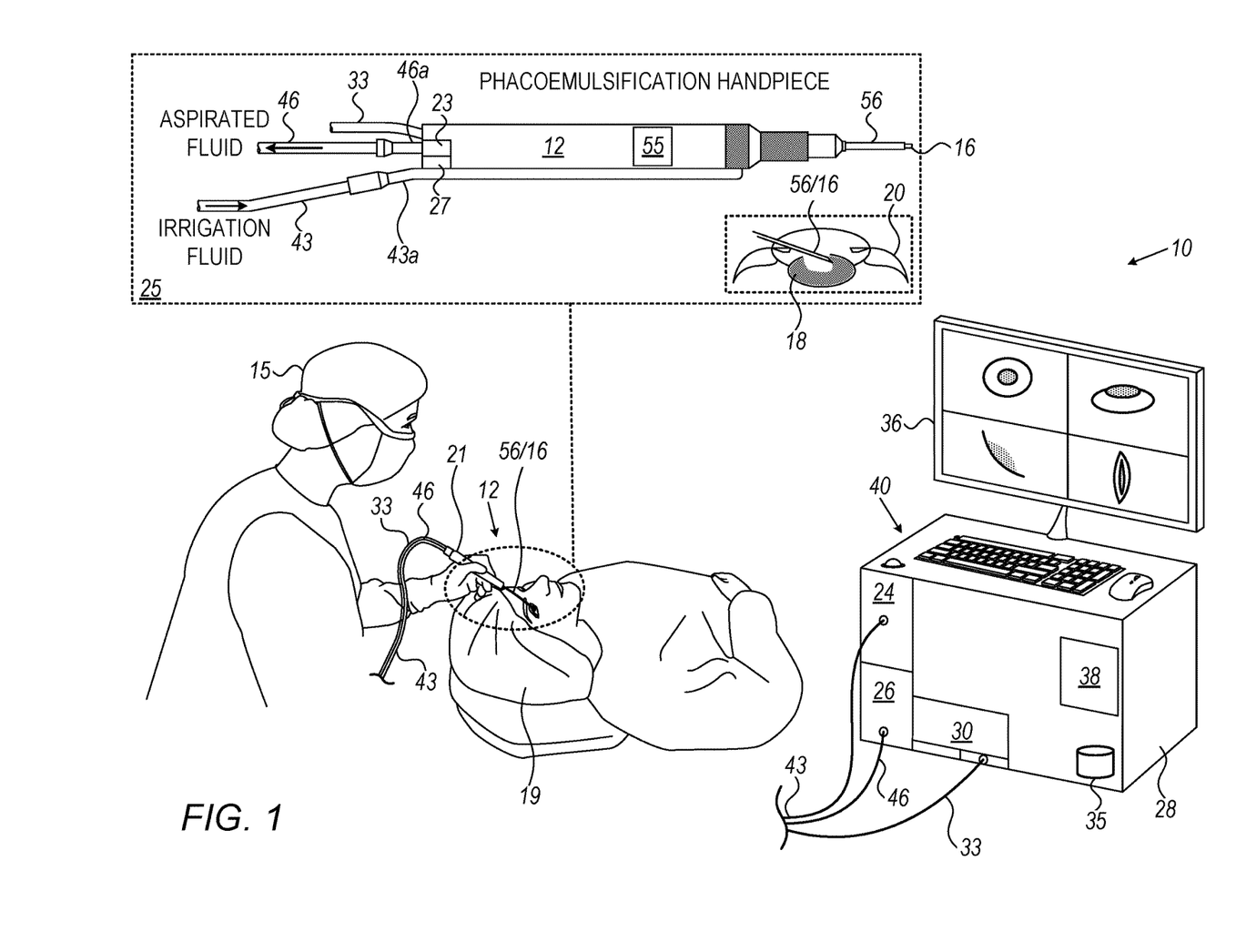
FIG. 1 is a schematic, pictorial view, along with a side view, of a phacoemulsification system, in accordance with an embodiment of the present invention.

FIG. 1 is a schematic, pictorial view, along with a side view, of a phacoemulsification system 10, in accordance with an embodiment of the present invention.

As seen in the pictorial view of phacoemulsification system 10, and in inset 25, phacoemulsification probe 12 (e.g., a handpiece 12) comprises a needle 16 surrounded by an irrigation sleeve 56. Needle 16 is hollow and its lumen is used as an aspiration channel.

Needle 16 is configured for insertion into a lens capsule 18 of an eye 20 of a patient 19 by a physician 15 to remove a cataract. The needle (and irrigation sleeve 56) are shown in inset 25 as a straight object. However, any suitable needle may be used with phacoemulsification probe 12, for example, a curved or bent tip needle commercially available from Johnson & Johnson Surgical Vision, Santa Ana, CA, USA.

In the shown example, probe 12 includes a sensor 27 coupled with irrigation channel 43a, and a sensor 23 coupled with aspiration channel 46a. Channels 43a and 46a are coupled respectively to irrigation line 43 and aspiration line 46. Sensors 23 and 27 may be any sensor known in the art, including, but not limited to, a vacuum sensor or flow sensor. The sensor measurements (e.g., pressure, vacuum, and/or flow) are taken close to the proximal end of the handpiece where the irrigation outlet and the aspiration inlet are located, so as to provide processor 38 an accurate indication of the actual measurements occurring within an eye and provide a short response time to a control loop comprised in processor 38.

A sensor as discussed herein includes types of pressure sensors that are configured to provide sufficiently accurate measurements of low sub-atmospheric pressures within a typical sub-pressure range at which aspiration is applied (e.g., between 1 mmHg and 650 mmHg). In an embodiment, the same pressure sensor model is used to measure irrigation pressure and aspiration sub-pressure, using different sensor settings/calibrations.

As shown, during the phacoemulsification procedure, a processor-controlled pump 24 comprised in a console 28 pumps irrigation fluid from an irrigation reservoir or tank (shown in FIG. 2) via irrigation sleeve 56, to irrigate the eye. The fluid is pumped via irrigation tubing line 43 running from console 28 to probe 12. Irrigation pump 24 may be any pump known in the art, for example, a peristaltic pump, and, using sensors (e.g., as indicated by sensors 23 and/or 27), processor 38 controls an irrigation pump 24 rate to maintain intraocular pressure within prespecified limits.

Eye fluid and waste matter (e.g., emulsified parts of the cataract) are aspirated via hollow needle 16 to a collection receptacle (not shown) by a processor-controlled aspiration pump 26 also comprised in console 28 and using aspiration tubing line 46 running from probe 12 to console 28. In an embodiment, processor 38 controls an aspiration rate of aspiration pump 26 to maintain intraocular pressure (in case of sub-pressure indicated, for example, by sensor 27) within prespecified limits.

In other embodiments, a processor-controlled bypass valve and/or an aspiration blocking valve may be used with the sensors to maintain intraocular pressure within prespecified limits. For example, a system to reduce a vacuum surge is described in U.S. patent application Ser. No. 17/130,409, filed Dec. 22, 2020, and titled, "A Module for Aspiration and Irrigation Control," whose disclosure is incorporated herein by reference.

As further shown, phacoemulsification probe 12 includes a piezoelectric crystal 55, coupled to a horn (not shown), that drives needle 16 to vibrate in a resonant vibration mode that is used to break a cataract into small pieces during a phacoemulsification procedure. Console 28 comprises a piezoelectric drive module 30, coupled with the piezoelectric crystal, using electrical wiring running in cable 33. Drive module 30 is controlled by processor 38, to, for example, maintain needle 16 at maximal vibration amplitude. The drive module may be realized in hardware or software, for example, in a proportional-integral-derivative (PID) control architecture.

Processor 38 may receive user-based commands via a user interface 40, which may include setting a vibration mode and/or frequency of the piezoelectric crystal, and setting or adjusting an irrigation and/or aspiration rate of the irrigation pump 24 and aspiration pump 26. Processor 38 may receive user-based commands via a user interface 40, which may include needle 16 stroke amplitude settings and turning on irrigation and/or aspiration. In an embodiment, the physician uses a foot pedal (not shown) as a means of control. For example, pedal position one activates only irrigation, pedal position two activates both irrigation and aspiration, and pedal position three adds needle 16 vibration. Additionally, or alternatively, processor 38 may receive the user-based commands from controls located in a handle 21 of probe 12.

In an embodiment, user interface 40 and display 36 may be integrated into a touch screen graphical user interface.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements, which are omitted for clarity of presentation. For example, physician 15 typically performs the procedure using a stereo microscope or magnifying glasses, neither of which are shown. Physician 15 may use other surgical tools in addition to probe 12, which are also not shown in order to maintain clarity and simplicity of presentation.

Iop Reduction Simulation Jig

Figure 2:
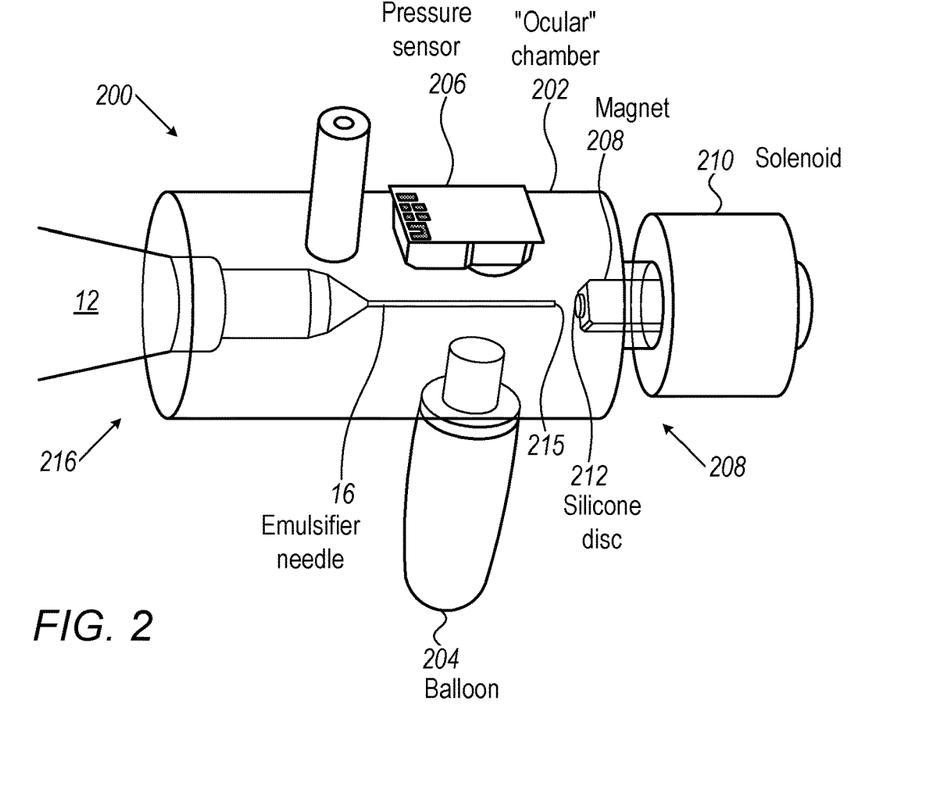
FIG. 2 is an orthogonal projection schematically describing a jig that simulates pressure-time changes to an eye due to phacoemulsification occlusion and occlusion-release, in accordance with an embodiment of the present invention.

FIG. 2 is an orthogonal projection schematically describing a jig 200 that simulates pressure-time changes to an eye due to phacoemulsification occlusion and occlusion-release, in accordance with an embodiment of the present invention. Jig 200 is used with a phacoemulsification simulation apparatus (e.g., a lab setup) of FIG. 3 below, to design a phacoemulsification system that minimizes risk of a vacuum surge occurring during phacoemulsification.

Jig 200 comprises a closed chamber, in the present example a cylinder 202 (called an "ocular" chamber) filled with fluid to serve as an eye model, into which needle 16 of phacoemulsifier 12 is inserted. A flexible balloon 204 is connected to the cylinder 202, and the combination may be filled with fluid simulating the aqueous humor and emulsified lens of the eye. A pressure sensor 206 measures the pressure of the fluid in cylinder 202 to simulate IOP.

A phacoemulsifier holder 216 is configured have a needle of phacoemulsifier 12 inserted into chamber 202. Place holder 216 also mechanically supports phacoemulsifier 12 in place with jig 200.

An occlusion/occlusion-release trigger device 208 is configured to replicate, as closely as possible, the pressure changes with time that occur during the formation and release of an actual occlusion. To this end, trigger device 208 comprises an activating solenoid 210, a magnet 214 that is moved linearly by solenoid 210, and a silicone disc 212 attached to magnet 214. The magnet and disc are aligned with an inlet 215 of needle 16. A processor (shown in FIG. 3 below) controls solenoid 210 in order to simulate the blocking and unblocking of inlet 215 during formation and release of an occlusion.

An obstruction, and freeing of the obstruction, may be simulated by operating the solenoid 210 to close the inlet with the disc 212, and then operating the solenoid 210 to open the inlet by removing the disc 212. Moreover, a driver of the solenoid (seen in FIG. 3) is used with a driving waveform that mimics a rapid but sufficiently gentle occlusion, in terms of a mechanical impulse exerted on needle 16, in order to recreate the actual temporal pressure profile of an occlusion. Pressure changes in cylinder 202 (the "eye model") during this simulation are measured by sensor 206.

Figure 3:
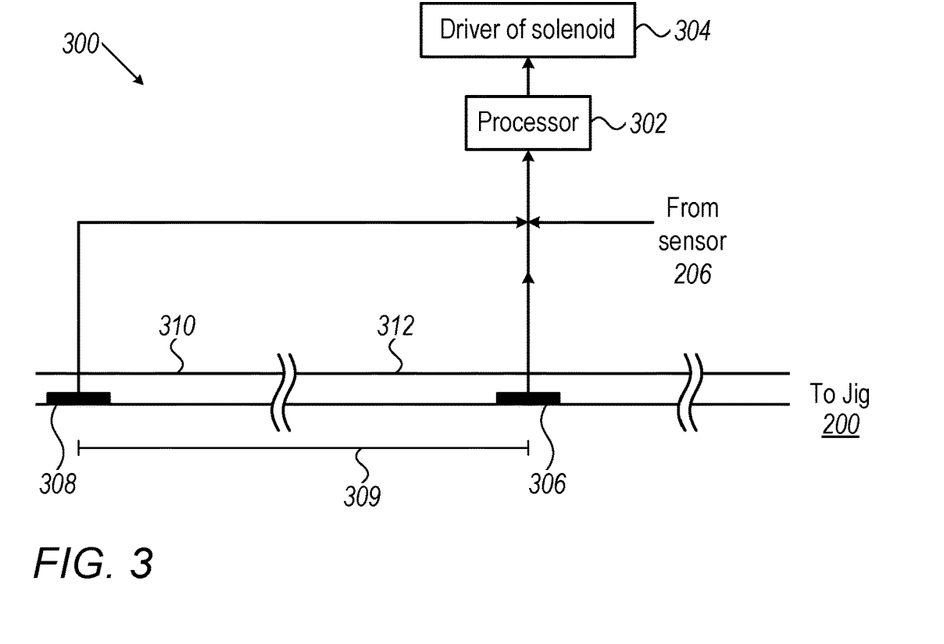
FIG. 3 is block diagram schematically describing a lab setup to simulate pressure-time changes to an eye using the jig of FIG. 2, in accordance with an embodiment of the present invention.

FIG. 3 is block diagram, schematically describing a lab setup 300 to simulate pressure-time changes to an eye using jig 200 of FIG. 2, in accordance with an embodiment of the present invention.

In the shown embodiment, setup 300 is shown schematically to simulate a situation where an occlusion-release occurs in a needle of a handpiece, and is detected by either a first, distal, sensor in the vicinity of the handpiece or by a second, proximal, sensor (e.g., in a console).

To this end, a first sensor 306, similar to sensor 23 of FIG. 1, is coupled with aspiration channel 46a. A second sensor 308 is coupled with aspiration line 46, for example in console 24 of FIG. 1. Sensors 306 and 308 may be any sensor known in the art, including, but not limited to, a vacuum sensor or flow sensor. The two sensors are separated by a tubing length 309 that can be of any length, including several meters long.

A processor 302 controls a driver 304 of solenoid 210 of jig 200. Processor 302 is configured to drive solenoid 210 to initiate occlusion or occlusion-release at a known timing. Processor 302 is further configured to receive readings, such as pressure readings, from sensors 206, 306 and 308 over time. In some embodiments, readings from only sensor pairs 306 and 308, or sensor pairs 206 and 308, are used.

Typically, processor 302, which can be processor 38 of FIG. 1, controls an aspiration pump and/or valves, which the processor can trigger either to response to readings from 306 or 308 to mitigate pressure changes, such as a vacuum surge.

Processor 302 produces pressure profiles in time for various scenarios, such as a scenario in which sensor 306 is available in a phacoemulsification system, or a scenario in which only sensor 308, which is some distance away from handpiece 12, is available in a phacoemulsification system. Typically, the processor measures delay time between lowest pressure values (i.e., maximal vacuum surge readings) of the measurements.

Typical simulations using lab setup 300 (e.g., a phacoemulsification simulation apparatus) show that processor 302 can initiate valve response to vacuum surge in less than 4 ms using readings from sensor 306, as opposed to tens of milliseconds using readings from sensor 308. Moreover, simulations using lab setup 300 show that response by a distal valve (not shown), located in the vicinity of handpiece 12 to block aspiration channel 46a in response to a reading from sensor 306, may eliminate a vacuum surge. Simulations using lab setup 300 show that other solutions, such as using pumps or other valves, demonstrate different levels of reduction in vacuum surge, depending on the simulated system. For example, using an aspiration pump alone cuts vacuum surge duration time to roughly 100-150 ms, compared to 400 ms in current systems.

The apparatus shown in FIG. 3 is brought by way of example. In another embodiment, the apparatus is coupled to an electromechanical syringe (not shown), that generates a pressure wave in aspiration line 46. In this case, the processor measures delay time between highest pressure values (i.e., maximal pressure readings) of the measurements.

Figure 4:
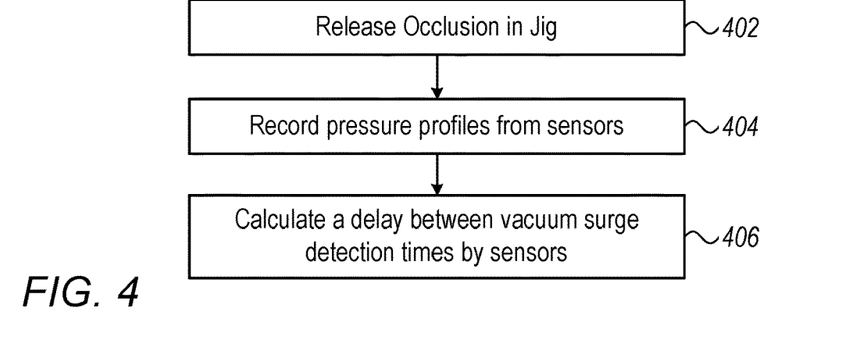
FIG. 4 is a flow chart schematically illustrating a method for simulating pressure-time changes to an eye using the lab setup of FIG. 3 and the jig of FIG. 2, in accordance with an embodiment of the present invention.

FIG. 4 is a flow chart schematically illustrating a method for simulating pressure-time changes to an eye using lab setup 300 of FIG. 3 and jig 200 of FIG. 2, in accordance with an embodiment of the present invention. The process begins with processor 302 commanding, for example, an occlusion-release in jig 200, by moving disc 212 away from the inlet 215 of needle 16, at an occlusion releasing step 402.

At a pressure profile recording step 404, processor 302 receives and records real-time pressure readings from sensors 306 and 308, or from sensors 206 and 308, or sensors 206 and 306. In the latter two cases, one of sensors 306 and 308 can be redundant.

At a vacuum surge detection time delay step 406, processor 302 calculates, for example by analyzing pressure waveforms the processor generated from the two sensor readings, a time delay between the detection made by sensor 306 and that made by sensor 308, for a given distance 309 between the sensors.

Needle Vibration Simulation Jig

As noted above, a stroboscope may be used to visualize the movement of the distal tip (e.g., needle) of a phacoemulsifier needle inside a windowed jig that serves as an eye model. However, the tip movement causes cavitation in the surrounding liquid, and the cavitation generates bubbles which may block the stroboscope light, for example by attaching to the viewing windows of a jig.

Figure 5:
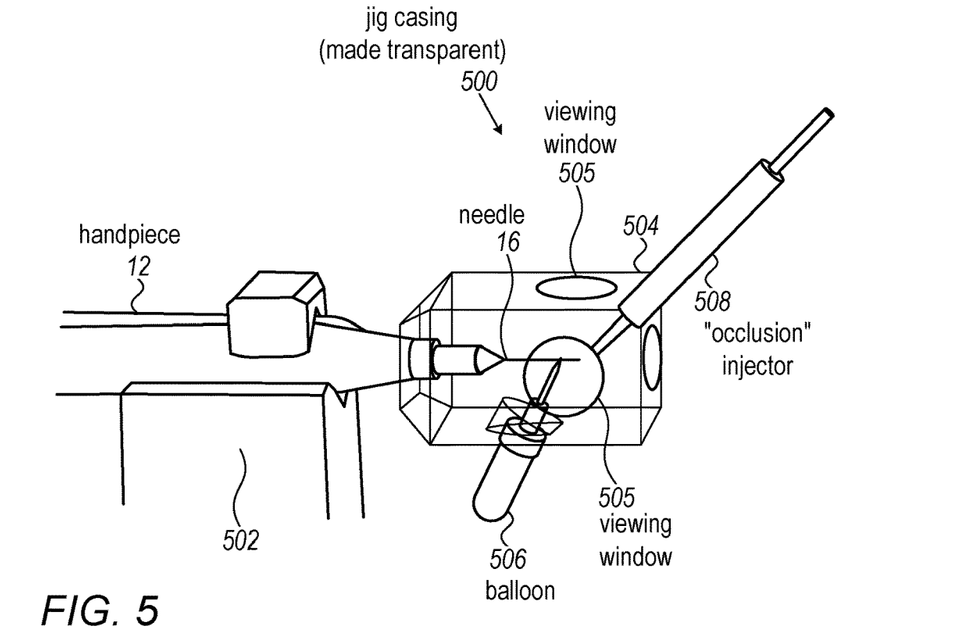
FIG. 5 is an orthogonal projection schematically describing a windowed jig comprising a fluid-filled balloon configured to enable imaging phacoemulsification needle vibration inside the windowed jig, in accordance with an embodiment of the present invention.

FIG. 5 is an orthogonal projection schematically describing a windowed-jig 500 comprising a fluid filled balloon 506 configured to enable imaging vibration of phacoemulsification needle 16 inside windowed-jig 500, in accordance with an embodiment of the present invention.

Jig 500 comprises a closed compartment 504 (called a jig casing) filled with fluid to serve as an eye model, into which is inserted needle 16 of phacoemulsifier 12 that is held by a mount 502. Windows 505 allow the use of a stroboscope (not shown) to visualize the vibration of needle 16. An occlusion injector 508 may be used to inject particles to block aspiration by needle 16.

A flexible balloon 506 is connected to the windowed-jig 500, and the combination is filled with fluid simulating the aqueous humor and emulsified lens of the eye. When required, pressing balloon 506 generates flow that moves the bubbles away from the path followed by the stroboscope light.

The jig of FIG. 5 is brought purely by way of example, to present the concept. For example, other devices than the balloon, that act as flow generators, may be used to remove the bubbles, including a piston (e.g., a syringe) or a pump.

Figure 6:
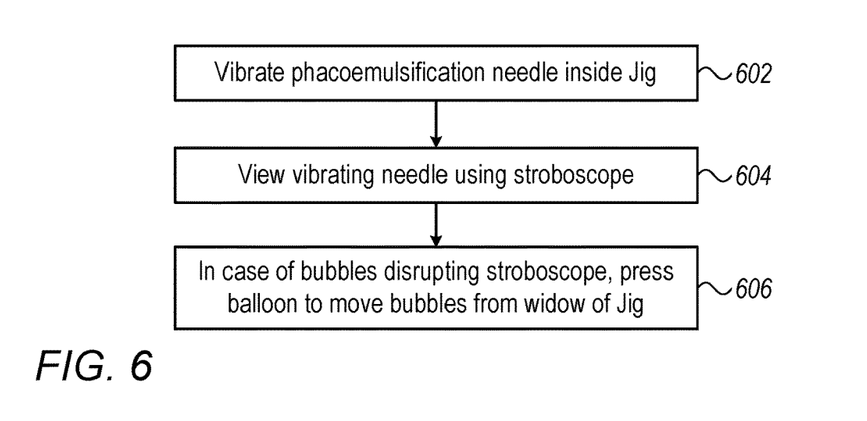
FIG. 6 is a flow chart schematically illustrating a method for imaging phacoemulsification needle vibration using the jig of FIG. 5, in accordance with an embodiment of the present invention.

FIG. 6 is a flow chart schematically illustrating a method for imaging phacoemulsification needle vibration using jig 500 of FIG. 5, in accordance with an embodiment of the present invention.

The process begins with processor vibrating phacoemulsification needle 16 inside jig 500, at a needle vibration step 602.

At a vibration imaging step 604, the vibration (e.g., its trajectory) is imaged (e.g., viewed) using a stroboscope that illuminates the needle via window 505 of the jig.

At a clearing view step 606, in case bubbles accumulate on window 505 disrupting stroboscope illumination or bubbles accumulate in a field of view of the stroboscope, balloon 506 is pressed to generate flow that removes the bubbles.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification simulation apparatus, comprising:
   a trigger device configured to apply, to fluid at an inlet of a needle of a phacoemulsifier, a pressure profile as a function of time in response to an input waveform;
   at least two sensors, configured to measure a pressure of the fluid at respective points in the phacoemulsification simulation apparatus; and
   a processor, which is configured to:
      drive the trigger device with the input waveform, thereby causing the trigger device to apply the pressure profile to the inlet while the fluid is aspirated via an aspiration line;
      receive measurements of the pressure of the fluid from the at least two sensors; and
      analyze an aspiration performance of the phacoemulsifier in response to the measurements.

2. The phacoemulsification simulation apparatus according to claim 1, wherein the trigger device comprises a piston.

3. The phacoemulsification simulation apparatus according to claim 1, further comprising a chamber configured to be filled with the fluid and to receive the needle of the phacoemulsifier fluidly coupled with the aspiration line, wherein the trigger device is fitted within the chamber and configured to apply the pressure profile by applying to the needle a blockage profile as a function of time in response to the input waveform.

4. The phacoemulsification simulation apparatus according to claim 3, wherein one of the at least two sensors are coupled with the chamber.

5. The phacoemulsification simulation apparatus according to claim 3, further comprising a balloon in fluid communication with the chamber.

6. The phacoemulsification simulation apparatus according to claim 3, wherein one of the at least two sensors is coupled with the phacoemulsifier.

7. The phacoemulsification simulation apparatus according to claim 3, wherein one of the at least two sensors is coupled with the aspiration line.

8. The phacoemulsification simulation apparatus according to claim 1, wherein the processor is configured to analyze the aspiration performance by calculating a time delay between one of respective lowest-pressure and highest-pressure values in the measurements received from the at least two sensors.

9. A phacoemulsification simulation method, comprising:
   in a phacoemulsification simulation system, applying, to fluid at an inlet of a needle of a phacoemulsifier, a pressure profile as a function of time in response to an input waveform, by driving a trigger device with the input waveform while the fluid is aspirated via an aspiration line;
   using at least two sensors, measuring a pressure of the fluid at respective points in the phacoemulsification simulation system; and
   analyzing an aspiration performance of the phacoemulsifier in response to the measurements.

10. The phacoemulsification simulation method according to claim 9, wherein the trigger device comprises a piston.

11. The phacoemulsification simulation method according to claim 9, wherein applying the pressure profile comprises applying to the needle a blockage profile as a function of time in response to the input waveform.

12. The phacoemulsification simulation method according to claim 9, wherein analyzing the aspiration performance comprises calculating a time delay between one of respective lowest-pressure and highest-pressure values in the measurements received from the at least two sensors.

\* \* \* \* \*